(12) United States Patent
Rizoiu et al.

(10) Patent No.: US 8,002,544 B2
(45) Date of Patent: Aug. 23, 2011

(54) FLUID CONTROLLABLE LASER ENDODONTIC CLEANING AND DISINFECTING SYSTEM

(75) Inventors: Ioana M. Rizoiu, San Clamente, CA (US); Peter Chueh, Tustin, CA (US); Jeffrey W. Jones, Robertson, WY (US); Dmitri Boutoussov, Dana Point, CA (US)

(73) Assignee: Biolase Technology, Inc., Irvine, CA (US)

( * ) Notice: Subject to any disclaimer, the term of this patent is extended or adjusted under 35 U.S.C. 154(b) by 535 days.

(21) Appl. No.: 12/142,656

(22) Filed: Jun. 19, 2008

(65) Prior Publication Data
US 2009/0042171 A1 Feb. 12, 2009

Related U.S. Application Data (60) Provisional application No. 61/036,971, filed on Mar. 16, 2008, provisional application No. 61/036,465, filed on Mar. 13, 2008, provisional application No. 61/036,972, filed on Mar. 16, 2008, provisional application No. 61/034,982, filed on Mar. 9, 2008, provisional application No. 61/030,976, filed on Feb. 24, 2008, provisional application No. 61/049,544, filed on May 1, 2008, provisional application No. 61/012,446, filed on Dec. 9, 2007, provisional application No. 60/995,759, filed on Sep. 28, 2007, provisional application No. 60/994,891, filed on Sep. 21, 2007, provisional application No. 60/994,723, filed on Sep. 20, 2007, provisional application No. 60/994,571, filed on Sep. 19, 2007, provisional application No. 60/961,113, filed on Jul. 18, 2007, provisional application No. 60/936,473, filed on Jun. 19, 2007.

(51) Int. Cl.
*A61C 1/00* (2006.01)

(52) U.S. Cl. ............................................ 433/29; 433/81
(58) Field of Classification Search .................... 433/29, 433/224, 81, 89; 606/10–19
See application file for complete search history.

(56) References Cited

U.S. PATENT DOCUMENTS
4,995,403 A 2/1991 Beckman et al.
(Continued)

FOREIGN PATENT DOCUMENTS
JP 5200045 A 8/1993
(Continued)

OTHER PUBLICATIONS
International Search Report, Jan. 2, 2009, PCT/US2008/067533.

*Primary Examiner* — Cris L Rodriguez
*Assistant Examiner* — Eric Rosen
(74) *Attorney, Agent, or Firm* — Stout, Uxa, Buyan & Mullins, LLP (57) ABSTRACT

An endodontic probe is used to perform disinfection procedures on target tissues within root canal passages and tubules. The endodontic probe can include an electromagnetic radiation emitting fiber optic tip having a distal end and a radiation emitting region disposed proximally of the distal end. According to one aspect, the endodontic probe can include a porous structure that encompasses a region of the fiber optic tip excluding the radiation emitting region and that is loaded with biologically-active particles, cleaning particles, biologically-active agents, or cleaning agents for delivery from the porous structure onto the target tissues. Another aspect can include provision of the endodontic probe with an adjustable channel-depth indicator, which encompasses a region of the fiber optic tip besides the radiation emitting region and which is movable in proximal and distal directions along a surface of the fiber optic tip to facilitate the provision of depth-of-insertion information to users of the endodontic probe.

18 Claims, 3 Drawing Sheets

U.S. PATENT DOCUMENTS

| | | |
|---|---|---|
| 5,228,852 A | 7/1993 | Goldsmith et al. |
| 5,570,182 A | 10/1996 | Nathel et al. |
| 5,997,296 A | 12/1999 | Schuldink |
| 6,607,524 B1 | 8/2003 | LaBudde et al. |
| 6,669,685 B1 | 12/2003 | Rizoiu et al. |
| 7,306,459 B1 | 12/2007 | Williams et al. |
| 2003/0068827 A1 | 4/2003 | Morris et al. |
| 2003/0100824 A1 | 5/2003 | Warren et al. |
| 2005/0123878 A1 | 6/2005 | Lee |
| 2007/0031777 A1* | 2/2007 | Wang et al. .................... 433/29 |

FOREIGN PATENT DOCUMENTS

| | | |
|---|---|---|
| JP | 5506601 A | 9/1993 |
| JP | 11511386 A | 10/1999 |

* cited by examiner

FLUID CONTROLLABLE LASER ENDODONTIC CLEANING AND DISINFECTING SYSTEM

This invention claims the benefit of Prov. App. 61/036,971, file Mar. 16, 2008, entitled ENDODONTIC ADJUSTABLE CHANNEL-DEPTH INDICATOR; Prov. App. 61/036,465, file Mar. 13, 2008, entitled ENDODONTIC ADJUSTABLE PROBE-DEPTH INDICATOR; Prov. App. 61/036,972, file Mar. 16, 2008, entitled FLUID CONTROLLABLE LASER ENDODONTIC CLEANING AND DISINFECTING SYSTEM; Prov. App. 61/034,982, file Mar. 9, 2008, entitled FLUID CONTROLLABLE LASER ENDODONTIC CLEANING AND DISINFECTING SYSTEM; Prov. App. 61/030,976, file Feb. 24, 2008, entitled FLUID CONTROLLABLE LASER ENDODONTIC CLEANING AND DISINFECTING SYSTEM; Prov. App. 61/049,544, file May 1, 2008, entitled CANNULA ENCLOSING RECESSED WAVEGUIDE OUTPUT TIP; Prov. App. 61/012,446, file Dec. 9, 2007, entitled CANNULA ENCLOSING RECESSED WAVEGUIDE OUTPUT TIP; Prov. App. 60/995,759, file Sep. 28, 2007, entitled PROBES AND BIOFLUIDS FOR TREATING AND REMOVING DEPOSITS FROM TISSUE SURFACES; Prov. App. 60/994,891, file Sep. 21, 2007, entitled PROBES AND BIOFLUIDS FOR TREATING AND REMOVING DEPOSITS FROM TISSUE SURFACES; Prov. App. 60/994,723, file Sep. 20, 2007, entitled PROBES AND BIOFLUIDS FOR TREATING AND REMOVING DEPOSITS FROM TISSUE SURFACES; Prov. App. 60/994,571, file Sep. 19, 2007, entitled PROBES AND BIOFLUIDS FOR TREATING AND REMOVING DEPOSITS FROM TISSUE SURFACES; Prov. App. 60/961,113, file Jul. 18, 2007, entitled ENDODONTIC DISINFECTION; Prov. App. 60/936,473, file Jun. 19, 2007, entitled ROOT CANAL DECONTAMINATION, the contents of all which are expressly incorporated herein by reference.

This application is related to application Ser. No. 11/800,184, entitled MODIFIED-OUTPUT FIBER OPTIC TIPS; Int. App. PCT/US08/52106, entitled MODIFIED-OUTPUT FIBER OPTIC TIPS; application Ser. No. 11/330,388, entitled FLUID CONDITIONING SYSTEM; application Ser. No. 11/033,441, entitled MODIFIED-OUTPUT FIBER OPTIC TIPS; U.S. Pat. No. 7,270,657, entitled RADIATION EMITTING APPARATUS WITH SPATIALLY CONTROLLABLE OUTPUT ENERGY DISTRIBUTIONS; U.S. Pat. No. 7,108,693, entitled ELECTROMAGNETIC ENERGY DISTRIBUTIONS FOR ELECTROMAGNETICALLY INDUCED MECHANICAL CUTTING; and U.S. Pat. No. 5,741,247, entitled USER PROGRAMMABLE COMBINATION OF ATOMIZED PARTICLES FOR ELECTROMAGNETICALLY INDUCED CUTTING, the contents of all which are expressly incorporated herein by reference.

BACKGROUND OF THE INVENTION

1. Field of the Invention

The present invention relates generally to electromagnetic radiation procedural devices and, more particularly, to the use of electromagnetic radiation devices in medical applications.

2. Description of Related Art

A primary causative agent in pulpal and periapical pathosis is inadequate bacteria control. Research has shown that the absence of infection before obturation of a tooth undergoing endodontic treatment can result in a higher success rate, thus indicating the control or elimination of such intracanal pathogens to be advantageous to the generation of a favorable outcome for a given procedure.

The prior art has encompassed various endodontic treatments directed to the attenuation of bacterial counts and adverse symptoms from the root canal system, many being implemented in a relatively nonsurgical or low impact fashion. Typically, clinical endodontic procedures have relied on mechanical instrumentation, mechanical intracanal irrigants, and medicaments to disinfect the root canal system.

Prior-art instrumentation techniques involving hand and/or rotary instruments, as well as ultrasonic and sonic devices, have brought about some success in reducing bacterial loads in infected canals. While such instrumentation techniques of the prior art have not been altogether ineffective, they do tend to fall short of the goal of total or near total disinfection of the root canal system.

In the category of irrigants, agents such as sodium hypochlorite and chlorhexidine have been implemented in root canal disinfecting treatments with some degree of success. Such agents have been found to be capable, for example, of providing relatively useful antimicrobial effects in certain instances. Here, too, infection of the root canal and adjacent dentin may persist, however, following such applications, owing perhaps to an inability of these agents to reach all the infecting microorganisms.

Regarding the third mentioned category, of medicaments, the use of intracanal medications, such as calcium hydroxide, has typically been ineffective in the context of short-term applications. That is, longer term applications have frequently been indicated as a consequence, for example, of such agents failing to adequately address and eliminate endodontic infections by way of only a few applications. Consequently, such applications in the prior-art have typically required multiple applications, which in turn have required multiple patient visits. These multiple visits, while potentially increasing a rate of effective treatments in connection with medicaments such as calcium hydroxide, can increase treatment time and reduce patient compliance, thus increasing the risk of treatment failure.

Lasers, such as mid-infrared lasers including the Erbium, chromium:yttrium-scandiumgallium-garnet (Er,Cr:YSGG) laser, have been used in root canal procedures involving cleaning, shaping and enlarging of the root canal, as well as in osseous, apical and periodontal surgical procedures. The Er,Cr:YSGG laser is known to be capable of removing calcified hard tissues by emitting a beam of infrared energy at 2.78 μm in combination with an emitted water spray.

SUMMARY OF THE INVENTION

A laser having a high absorption for one or more predetermined fluids, which are disposed either around or adjacent to a target tissue or disposed within the target tissue, is implemented to achieve intra-passage or intracanal disinfection. The fluid can comprise water in typical applications, and the target tissue can comprise soft tissue such as that of a root canal wall in exemplary implementations of the invention. The laser can be operated to clean or disinfect tissue within the root canal in one mode in which an external source applies fluid to or in a vicinity of the target tissue or in another mode in which external fluid is not applied, the latter mode being capable of potentiating an effect of absorption of the laser energy or greater absorption of the laser energy by fluids within bacteria on or in the target tissue. In accordance with another feature of the present invention, radially emitting laser tips are used in the implementation of cleaning and disinfecting procedures of root canals. The radially emitting or side firing effects provided by these laser tips can facilitate, among other things, better coverage of the root canal walls in certain instances as compared, for example, to conventional, forward firing tips. Consequently, a probability that the emitted laser energy will enter dentinal tubules of the root canal can be augmented, thus increasing a disinfecting potential or efficacy of the system, whereby disinfection or cleaning of portions of dentinal tubules disposed at relatively large distances from the canal can be achieved or achieved more efficiently (e.g., during a smaller time window) or more reliably (e.g., yielding results with greater reproducibility).

According to one aspect of the present invention, an endodontic probe is used to perform disinfection of target tissues within root canal passages and tubules. The endodontic probe can comprise an electromagnetic radiation emitting fiber optic tip having a distal end and a radiation emitting region disposed proximally of the distal end, and can further comprise a porous structure encompassing a region of the fiber optic tip excluding the radiation emitting region. The porous structure can be loaded with biologically-active particles, cleaning particles, biologically-active agents, and/or cleaning agents that are structured to be delivered from the porous structure onto the target tissues.

Another feature of the present invention includes an endodontic probe for performing disinfection of target tissues within root canal passages and tubules, the endodontic probe comprising (a) an electromagnetic radiation emitting fiber optic tip having a distal end and a radiation emitting region disposed proximally of the distal end and (b) an adjustable channel-depth indicator encompassing a region of the fiber optic tip besides the radiation emitting region. The adjustable channel-depth indicator can be configured to be movable in proximal and distal directions along a surface of the fiber optic tip to provide, for example, depth-of-insertion information to a user of the endodontic probe.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

Any feature or combination of features described or referenced herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. Additional advantages and aspects of the present invention are apparent in the following detailed description and claims that follow.

DETAILED DESCRIPTION OF THE INVENTION

Reference is made to Prov. App. 60/961,113, which contains an article entitled The antimicrobial efficacy of the erbium, chromium:yttrium-scandium-gallium-garnet laser with radial emitting tips on root canal dentin walls infected with Enterococcus faecalis. The devices and methods disclosed and referenced herein are intended to relate to and build upon devices and methods disclosed, and referenced, in that article, in part or in whole, in any combination or permutation, with or without modification, as would be understood by one skilled in the art to be possible in view of this disclosure to be feasible or modifiable to be feasible.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not presumed, automatically, to be to precise scale in all embodiments. That is, they are intended to be examples of implementations of various aspects of the present invention and, according to certain but not all embodiments, to be to-scale. While, according to certain implementations, the structures depicted in these figures are to be interpreted to be to scale, in other implementations the same structures should not. In certain aspects of the invention, use of the same reference designator numbers in the drawings and the following description is intended to refer to similar or analogous, but not necessarily the same, components and elements. According to other aspects, use of the same reference designator numbers in these drawings and the following description is intended to be interpreted as referring to the same or substantially the same, and/or functionally the same, components and elements. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent accompanying this disclosure is to discuss exemplary embodiments with the following detailed description being construed to cover all modifications, alternatives, and equivalents of the embodiments as may fall within the spirit and scope of the invention as defined by the appended claims. It is to be understood and appreciated that the process steps and structures described herein do not cover a complete architecture or process, and only so much of the commonly practiced features and steps are included herein as are necessary to provide an understanding of the present invention. The present invention has applicability in the field of laser devices in general. For illustrative purposes, however, the following description pertains to a medical laser device and a method of operating the medical laser device to perform surgical functions.

A fiber optic tip emitting electromagnetic radiation, such as laser radiation, is used in root canal cleaning and/or treatment procedure(s) with fluid (e.g., conditioned fluid) being applied beforehand and/or simultaneously with the radiation. In certain implementations, the radiation and fluid can alternatively, or additionally, be applied intermittently and/or after the radiation.

Applications can include procedures within a body passage, such as the root canal of a tooth, a vessel (e.g., blood vessel), or an opening, cavity or lumen, within hard or soft tissue. Exemplary applications, more particularly, can include in-tissue (e.g., within lumens, be they preexisting or natural, pre-formed or formed in real-time as part of a procedure) treatments of necrotic and/or infected root canals, occluded (e.g., with one or more of films, layers, smear layers, plaque, calcified materials, and other functionally restricting or occluding components) arteries, infected and/or inflamed periodontal pockets around teeth, necrotic bone, etc.

Visual feedback architectures and techniques can be implemented, such as, for example, in the context of deep tissue procedures including, for instance, those involving drilling deep into hard tissues. In other embodiments, the procedure(s) described or referenced herein may comprise sub-procedures described or referenced herein, such as, for example, removal of biological tissue and/or biological fluids, treatment of tissues, cleaning of tissues, anesthetizing, disinfecting, flushing, etc., in any combination (each being applied with one or more of the radiation(s) and fluid(s)), and furthermore, combined with any of the above (or described or referenced herein) items or steps, in any combination or permutation. Also, any of the above (or described or referenced herein) items or steps may be implemented unitarily or duplicatively, with one or more types of radiation and with one or more kinds of components in or making up the fluid (e.g., conditioning agents in the fluid, such as disinfectant, disinfectant particles, other biologically-active particles, biopowders, etc.), in any combination or permutation, with each being applied using one or more of the mentioned, or described or referenced anywhere herein, radiation, fluid and steps.

"Fluid" (the term meaning fluid as described or referenced herein) is released in a canal from a probe, cannula, fiber optic tip, or other emitting device (the terms being used interchangeably herein). The fluid can be emitted, for example, at a distal end only or in another embodiment through a portion of a sidewall only, of the probe, and/or through a sponge like or porous material (as described or referenced herein) or from a porous material such as capillary tubing (e.g., glass) having any of the mentioned functional (emitting) locations or properties. In one implementation, when pressure is applied to the probe (e.g., at the fluid emitting location) the fluid is released. According to some implementations, the term "fluid" may be replaced or supplemented with the term(s) "powder," "agent" or "particulates" so that "fluid" would read "powder" or "fluid and/or powder, agent, or particulates." Implementations may comprise a seal around part or all of, for example, a distal end, of the probe that can be pealed back and/or that dissolves or melts, for example that dissolves and/or melts when exposed to heat or fluid(s) of or introduced within the probe and/or human body.

A viscosity can be greater than water (e.g., slightly viscous) or even more viscous that that (e.g., it can be controllable to control intensity/strength of shock waves). A higher viscosity can generate a greater shock wave and a relatively lower viscosity, less. Exemplary ranges of viscosity can comprise one or more of 0.1-1 cPoise (centipoise), 1-50 cPoise, 50-500 cPoise and 500-1,500 cPoise. In a typical implementation, fluid (e.g., liquid of a viscosity that may be varied) may be applied before lasing. The liquid may be applied, for example, to clean tissue, open small channels and crevices in lateral channel (e.g., following removal of vital pulp with all of the roots and when remove then the channels can have remnant organic material in them whereby it may desirous for cleaning-out and removal of such). Thus, a viscosity may be selected, in certain implementations, with the consideration that too much viscosity may not flow facilitate adequate or extensive entry of the fluid into end-parts of dentinal tubules. In one implementation, an application of liquid with relatively low viscosity can be applied and then one or more other applications of liquid with greater viscosity or viscosities (e.g., successively greater) may be implemented. In particular implementations, the fluid may be less viscous and/or provided with less surface tension (e.g., by way of, for example, a surfactant such as a detergent) and/or may be configured more for cleaning or flushing purposes in which, for instance, a relatively low viscosity may facilitate flow into dentinal tubules. Other examples may include an engineering and selection of similar or different (e.g., relatively more viscous) parameters for the fluid such as, for example, in a case of seeking to increase a disruptive effect on a tissue from the shock waves, increasing a relative viscosity of the fluid.

Regarding one implementation of the invention, in a liquid such as water, initial pulses of radiation can operate to generate a bubble (e.g., a gaseous bubble) and then additional pulses can operate to expand the bubble more and more until the pressure on the outside of the bubble (from the liquid) reaches a limit and the bubble collapses, which creates shock waves from the collapsing. It also creates a negative pressure from the collapse, whereby, also, the expanding of the bubble creates positive pressure, thus generating a "plunger" effect which can push and pull liquid into and out of the dentinal tubules. The viscosity adjusting and/or altering can thus control these parameters. The shock waves, for example, can clean and/or disrupt (e.g., remove) the tissue based upon the selections of parameters.

Although the bubble(s) may be relatively large, such as when a fiber optic tip is in the canal and the canal is filled with fluid, such as blood, other bubbles may be implemented, such as within the target tissue. For example, absorption of infrared (IR) energy by dentin, from the presence of hydroxide and interstitial water (dentin matrix and intratubular), can be harnessed for bubble expansion/collapse effects, too. Additionally, or alternatively, intratubular water within the target may be used for bubble expansion/collapse, for achieving "micropulse-induced sequential absorption" with the expansions and collapses of bubbles in water and water vapor media of or in proximity to the target. Regardless of the type or size of bubble(s), as disclosed or referenced, an aspect of the invention comprises coupling concomitant acoustic waves, or shock waves, from the expanding/collapsing bubble(s) with endodontic procedures to disrupt intratubular bacteria.

In some embodiments, particles (e.g., biopowders or biologically-active particles) can be provided within or in conjunction with the fluid, so that, for example, during expansion of the bubble the particles can migrate (e.g., be pushed) into dentinal tubules and then when the bubble collapses can be drawn (e.g., be pulled) out or in another (e.g., opposite) direction. According to other aspects or implementations, some of the particles may serve to ablate tissue during some modes of operation and some (e.g., including the same, other, and/or different types of particles, such as, for example, an antiseptic which could be or include Silver particles) can be left inside the dentinal tubules during or in connection with the same mode (e.g., sub-procedures) or other modes (e.g., sub-procedures) of operation.

Figures 1A, 1B:
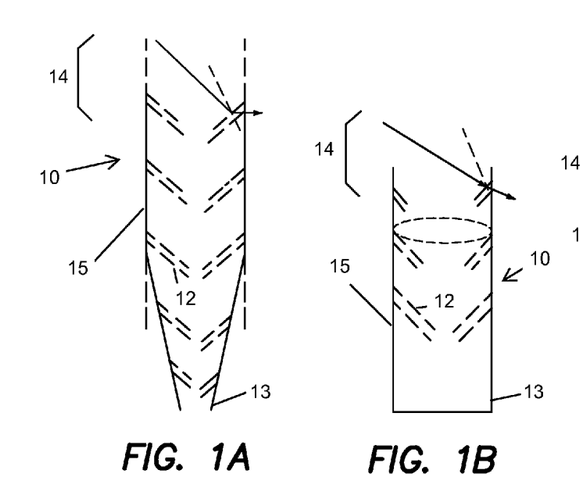
FIGS. 1A-1C are side-elevational views of various embodiments of side-firing fiber optic tips according to aspects of the present invention.
Figure 1C:
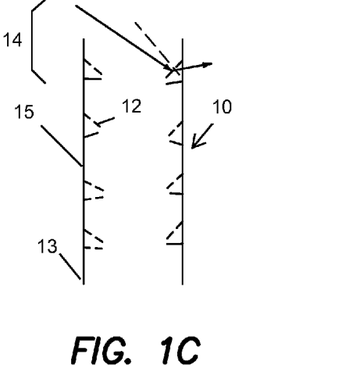

With reference to the drawings, in which like elements are indicated using like reference number designators, FIGS. 1A-1C are side-elevational views of various embodiments of side-firing fiber optic tips, probes, cannulas, or other emitting device (the terms being used interchangeably as mentioned above) 10 according to aspects of the present invention. As shown in phantom, one or more beam-altering elements 12 can be disposed in relation to the fiber optic tip 10 for changing one or more characteristics (e.g., reflection and/or refraction) of a beam propagating within (e.g., through) or in proximity to (e.g., external to and/or adjacent to a surface of) the fiber optic tip 10. Each of these figures contains an exemplary beam trace 14 including an internal incident beam solid line and a transmitted/refracted beam solid line tipped with an arrow head and further including a reflected-beam phantom line.

Each fiber optic tip 10 can comprise a distal end 13, a radiation emitting region disposed proximally of the distal end. e.g., at the arrow head part of the beam trace 14, a porous structure encompassing a region, e.g., 15, of the fiber optic tip 10 excluding the radiation emitting region(s), the porous structure 15 being loaded with one or more of biologically-active particles, cleaning particles, biologically-active agents, and cleaning agents that are structured to be delivered from the porous structure onto tissue, and a seal disposed over at least part of the porous structure, e.g., at 15, the seal being adhesively secured to the endodontic probe or constructed to be pealed away from the porous structure. The seal can be constructed to be removed while within a dentinal canal by operation of one or more of dissolving and melting.

The beam-altering elements 12 can be identical, similar, or divergent in one or more of physical (e.g., composition, dimension, or size) and functional characteristics, relative to one another. Each of the beam-altering elements 12 can comprise one or more of protuberances, coatings, notches, trenches, etched regions, cuts, and agents (e.g., having one or more characteristics different from that or those of the adjacent material of the fiber optic tip) formed over, onto, into and/or within an interior of, the side-firing fiber optic tip 10. The beam-altering elements 12 can have thicknesses, or depths, measured in a radial direction, within a range, for example, of about 1 micron to about one-half of a diameter, or in other embodiments about one-half of a radius, of the fiber optic tip 10, at the point of measurement thereof. In typical embodiments, beam-altering elements 12, such as, for example, those of FIGS. 1A and 1B, can have depths from about 1 micron to about 50 microns.

FIG. 1C depicts beam-altering elements 12 in the form of added or altered regions, such as filled trenches. In exemplary implementations, beam-altering elements 12, such as, for example, those of FIG. 1C, can have depths that range from about 50 microns to about 200 microns. With continued reference to FIG. 1C, the beam-altering elements 12 can comprise, for example, cuts that are filled (e.g., coated, deposited, or injected) with light altering material (e.g., high or low viscosity material). For instance, the light altering material may be instilled and/or formulated to scatter a distally-propagating beam as it exits (e.g., radially exits in a side-firing manner) the fiber optic tip 10.

Any one or more of the beam-altering elements 12 can in modified embodiments be configured with any one or more of a depicted or other regular geometric shape or of an irregular shape, and any one or more of a depicted or other patterned or non-patterned position relative to the fiber optic tip 10. In exemplary implementations, beam-altering elements 12 can be disposed on a single side (e.g., covering one-quarter of a circumference of the fiber optic tip) and/or at a single location along a single longitudinal portion (e.g., spanning a 2 mm distance) of the fiber optic tip 10. One or more of locations, orientations, shapes, dimensions, or other physically- or functionally-discernable characteristics of the beam-altering elements 12 can be adjusted to vary along a direction (e.g., a longitudinal direction) of the fiber optic tip 10. For example, the beam-altering elements 12 can be arranged to have depths or thicknesses that increase in the distal direction of the fiber optic tip 10. In another implementation, the beam-altering elements 12 can be engineered to have widths that increase along a distal direction of the fiber optic tip 10. According to yet another embodiment, the beam reflecting capabilities (e.g., to reflect distally traveling light in a radial or side-firing direction) of beam-altering elements 12 can be formed to vary (e.g., increase) in the distal direction of the fiber optic tip 10. Shapes of the fiber optic tips 10 (e.g., at outputting regions) can comprise tapered, cylindrical, conical, or any other shape described or referenced herein.

Figure 2:
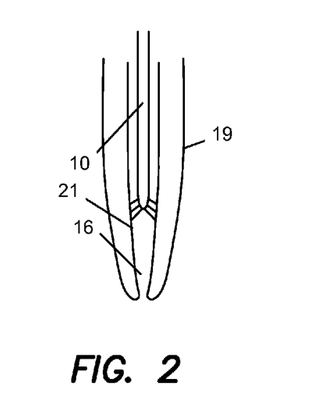
FIG. 2 depicts a side-firing fiber optic tip disposed within a root canal of a tooth.
Figure 3:
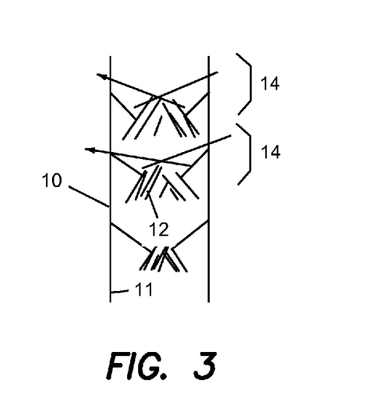
FIG. 3 provides a cross-sectional view, with beam traces, of a side-firing fiber optic tip.

FIG. 2 depicts a side-firing fiber optic tip 10 disposed in a root canal 16 of a tooth 19, and FIG. 3 elucidates a cross-sectional view of a side-firing fiber optic tip 10 with beam traces 14. The structures and techniques shown in FIG. 2 can correspond, for example, to those of FIGS. 6A and 6B. An exemplary implementation of the arrangement of FIG. 2 can comprise a shaped fiber optic tip 10 (e.g., a cone-shaped fiber optic tip) that delivers energy to a root canal wall 21 in radial, and/or in side-firing, directions only, or primarily in radial directions, or in directions at least parts of which comprise radial directions.

The beam-altering elements 12 of FIG. 3 are shown as cuts that form angles, e.g., 57 degree angles, relative to the optical axis of the fiber optic tip 10, and that allow for partial or total internal reflection of the distally traveling beam. Parts of the beam (e.g., in a central region of the fiber optic tip) that have not contacted any sidewalk 11 or beam-altering elements will tend to have primarily distally-directed components of travel. On the other hand, parts of the beam, as shown, which have already been reflected or refracted by one or more of sidewalk 11 and beam-altering elements 12 will tend to have, at least in part, directions of travel with non-distal (e.g., radial) components.

In the FIG. 3 illustration, these reflected or refracted beams can form, for example, conically-shaped, or wedge-shaped, beam traces 14 as they pass through openings corresponding to the non-presence of beam-altering elements. Thus, for example, the lines in FIG. 3 can be construed to represent three sets of beam-altering elements 12 disposed along a length of the fiber optic tip 10. The distal-most set, for example, is shown with cuts in left and right regions (e.g., an upper-left to lower-right extending cut and an upper-right to lower-left extending cut), and with two bands of light (e.g. a group of beams traveling from a central region between the two beam-altering elements in an upper-right to lower-left direction and another group of beams traveling from a central region between the two beam-altering elements in an a upper-left to lower-right direction).

Figures 4, 5A:
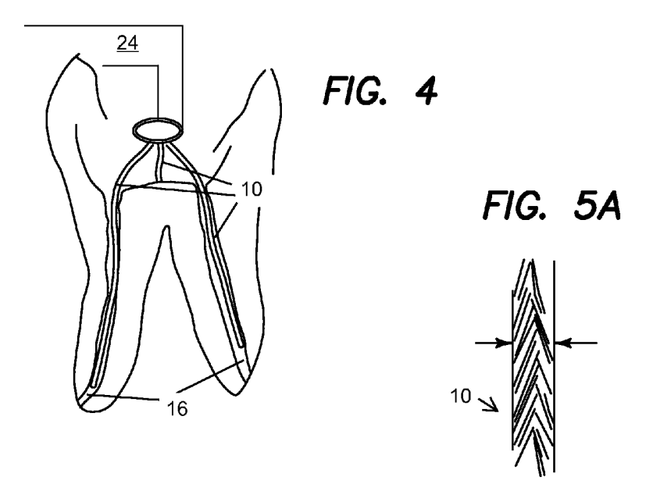
FIG. 4 depicts side-firing fiber optics and their fiber optic tips extending from a handpiece and branching into root canals of a tooth.
FIGS. 5A-5G are cross-sectional views of various embodiments of side-firing fiber optic tips, showing elements including arrangements of multi-fiber bundles within the side-firing fiber optic tips, according to multiple aspects of the present invention.

FIG. 4 depicts side-firing fiber optics 10, embodied as multi-fiber optics, or, alternatively, single fiber optics, extending from a handpiece 24 and branching into one or more root canals 16 and/or dentinal tubules, of a tooth.

FIGS. 5A-5G are cross-sectional views of various embodiments of side-firing fiber optic tips 10, showing elements including arrangements of multi-fiber bundles within the side-firing fiber optic tips 10, according to multiple aspects of the present invention.

Figure 5B:
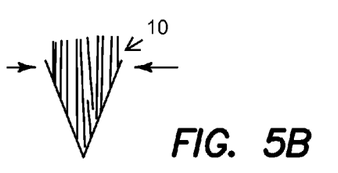
Figure 5C:
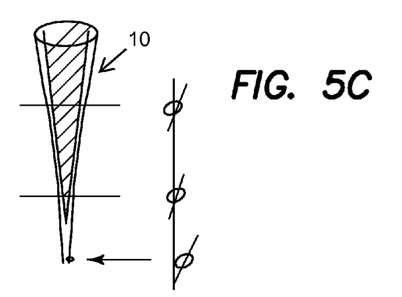
Figure 5D:
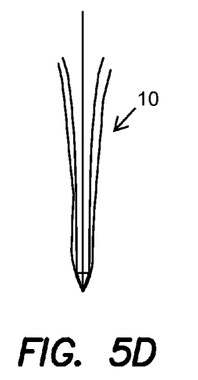
Figure 5E:
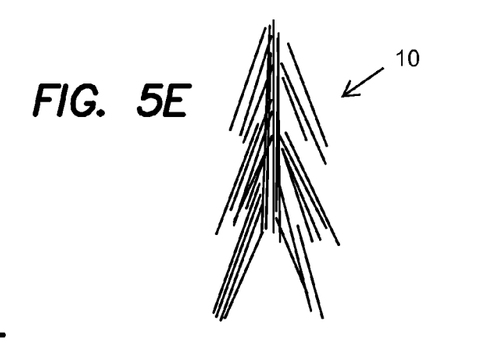

In FIGS. 5A and 5E, fibers or groups of fibers branch-off in the distal direction from a multi-fiber bundle that extends distally through the fiber optic tip 10. The depiction of FIG. 5E shows the branches, or greater concentrations of fibers, occurring or being formed at distinct levels along a length of the fiber optic tip 10.

Figure 5F:
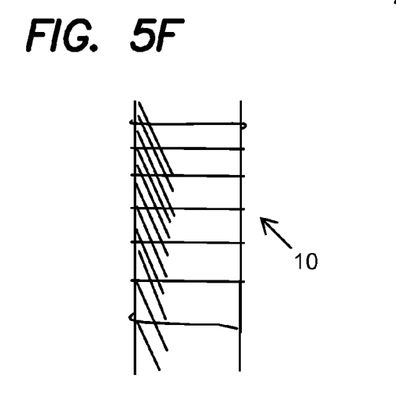
Figure 5G:
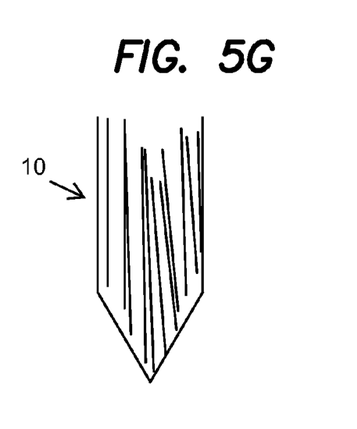

The architectures of FIGS. 5B and 5G comprise fibers of a multi-fiber bundle that travel generally in a direction parallel to an axis of the fiber optic tip 10 and that terminate (e.g., on one or more polished surfaces) at or on a shaped (e.g., radially-emitting or side-firing) surface, such as a beveled or conical surface, of a fiber optic tip 10. A beveled or conical surface of a fiber optic tip 10, such as shown in FIG. 5B, can comprise or be characterized by a tapering of about a 2% to 5% reduction in diameter of the fiber optic tip 10 with every mm in the distal direction. In one implementation, diameters of one or more fibers within the fiber optic tip 10 can increase (e.g. in a smooth, continuous, or regular fashion), along a distal direction, near the output ends of the fibers.

FIG. 5C shows a tapering fiber optic 10 with an outer or annular (e.g., ring-shaped) waveguide that converges into a circular (e.g., a "full" circle" that includes the interior, as distinguished from ring-shape) waveguide having, for example, a diameter of about 100 to about 400 microns. In one implementation, the area encompassed (e.g., surrounded by, or between) the outer waveguide can be hollow or solid. FIG. 5D shows a tapering fiber optic 10 with an outer or annular (e.g., ring-shaped) wall that encompasses, borders, or surrounds an interior waveguide. In one implementation, the area encompassed (e.g., surrounded by, or between) the outer waveguide can be hollow or solid. The structure of FIG. 5F shows beam-altering elements positioned along only one side of a fiber optic tip 10, to thereby provide a structure that side-fires from one side only or along only one radial direction (e.g., from left to right on the page of the figure).

Use of side-firing tips can increase the probability that the emitted laser radiation will enter dentinal tubules and have an effect on bacteria (e.g., to attenuate or eliminate endodontic infection) that are some distance from the canal. Distal ends or regions of the fiber output tips (e.g., side-firing tips and/or tips formed of glass, silica, or other optical materials, and in particular examples sapphire or quartz) can be formed with jackets or without jackets such as disclosed, for example, in the above referenced patents and patent applications.

Regarding the fluid and its components, one mode or sub-procedure can comprise a dry mode, which may be implemented, for example, before, during or after insertion of the probe and/or insertion of a fiber optic tip into the canal. As an example, a sponge can be provided on a probe and/or fiber optic tip with dry particles disposed thereon, for smearing on surfaces of the canal. The particles may comprise, for example, nanoparticles or microparticles and/or, in modified implementations, the mode(s) or sub-procedure(s) may or may not involve a non-fluid filled canal. The particles may be suspended in a dry and/or liquid (e.g., viscous) carrier. Furthermore, some or all of the particles may possess, for example, therapeutic (e.g., biologically-active particles) and/or cleaning properties. In addition to, or as an alternative to, the particles, therapeutic (e.g., biologically-active) and/or cleaning agents may be provided. In any of such modes or sub-procedures within the canal, wherein, for example, no water is present in dentinal tubules while the dentinal tubules remain moist with biological moisture, a sponge can be provided around a fiber with powder (e.g., comprising biopowders and/or particles) thereon or therein and the particles can be smeared onto canal structure as the fiber is advanced and retracted. Then, in one example, bubbles can be generated with, for example, provision of laser radiation and/or fluid (e.g., water), for expanding/collapsing bubbles, as described herein, to advance the particles into dentinal tubules. Hydroscopic type particles can be used, for example, which may be naturally drawn into the biological (e.g., fluid filled) dentinal tubules. The mode(s) or sub-procedure(s) may be performed before, after, or during, introduction of liquid into the dentinal tubules, and may be repeated, or interdispersed, in any order, with other mode(s) or sub-procedure(s).

Chemicals which can be implemented, at any point and in any described media, in the context of disinfection of the canal, may comprise, for example, in relatively concentrated or diluted compositions, one or more of: chlorehexidine gluconate, sodium chlorite (NAOCl), calcium hydroxide, an antibiotic (e.g. doxycycline, amoxycycline, etc.), hydrogen peroxide and other proxy type agents; solutions (e.g., aqueous and/or otherwise) containing ions, particles and/or nanoparticles (e.g., silver, salts, HA, etc.); solutions containing EDTA and combination of EDTA and various disinfectants; and others.

Laser radiation as described or referenced herein can be used in conjunction with hydrogels or nanocomposite biocompatible hydrogels. For example, such a composition can comprise one or more of nanoparticles, a matrix gel and an antibacterial agent. The antibacterial agent can comprise, for example, minocycline hydrochloride.

Implementations of the invention, in any form, combination, or permutation as described or referenced herein, may be used, for example, to treat surface conditions of the skin. In one implementation, the condition may comprise an acne condition. The agent used to treat the surface condition (e.g., acne) may comprise, for example, an antibacterial agent such as minocycline hydrochloride. Laser radiation can be delivered to, for example, a hydrogel and/or other type of gel that contains an antibacterial agent, from above the surface that contains the gel or from within the gel (e.g., via a probe or fiber optic placed within the gel).

The laser radiation can comprise, for example, a wavelength that is strongly absorbed in water and/or OH. Exemplary wavelengths may comprise those generated from Erbium and/or other lasers such as other infrared (IR) lasers, including, for examples, those having wavelengths falling within one or more of a of 400 nm to 550 nm wavelength range and a 750 to 1,100 nm wavelength range. Implementations of any one or more of the preceding aspects, taken alone or with any one or more of the following aspects, in any operable (or modified to be operable) form, combination, or permutation, as described or referenced herein, are contemplated and intended to fall within the scope of the current invention.

When the probe or fiber is used in a canal, such as in the context of an in-tissue or deep-tissue treatment, the probe or fiber can incorporate a stopper/plug device that will prevent fluids from escaping the canal, or being redistributed in an undesired temporal or positional fashion, during a treatment such as during application of laser irradiation.

This structure and technique can thus operate to create, for example, a confined environment for the laser to produce a higher pressure bubble/shockwave than would be present in an unconfined lumen or canal. The stopper/plug can be formed, for example, of rubber or other pliable or moldable material, for a complete seal, or may be formed, in whole or in part of a sponge or sponge-like (e.g., porous or semi-porous) material having, for example, one or more predetermined characteristics such as a predetermined permeability. The degree of permeability may be selected, for example, to allow for a predetermined, predictable, model-able, and/or controlled, at least in part, release of pressure (and/or agent, composition, or other material) corresponding to the number, size, distribution, and/or shapes of pores of the sponge. Furthermore, in any implementation described herein, the stopper/plug may be formed of a material that is transparent to one or more wavelengths of electromagnetic energy, such as that of cutting laser radiation or of an aiming beam being used, or other radiation such as illuminating visible light. For instance, the stopper/plug may comprise one or more of a non-opaque, transparent, clear, and see-through material.

Moreover, the stopper/plug can be (a) formed, in whole or in part, at one or more of a time beforehand and during a procedure, (b) assembled, in whole or in part, at one or more of a time beforehand and during a procedure, and/or (c) affixed to one or more of the body passage, lumen, or the probe or fiber, in whole or in part, at one or more of a time beforehand and during a procedure.

Furthermore, the probe may be formed, in whole or in part, and/or affixed to the probe or fiber, in whole or in part, from a liquid or gelatinous state using an injection and/or thickening/gelling or solidifying technique to form (in whole or in part) the stopper/plug, to affix (in whole or in part) the stopper/plug to the probe or fiber, and/or to position (in whole or in part) the stopper/plunge within the body passage.

According to another aspect of the invention, the probe or fiber can incorporate markings to indicate distance/depth (e.g., viewable directly or with an imager) for, as an example aiding with the insertion of the probe or fiber into a body passage or canal (e.g., deep canal). In further implementations, the probe or fiber can be motor driven or maneuverable/configurable to allow for movement (e.g., manual, semi-automatic, and/or automated) movement of the probe or fiber in one or more of an up-and-down, an in-and-out, a side-to-side, and a circumferential manner. The movement (e.g., automatic or pre-choreographed movement) can be coupled with or controlled by a computer program for enhancing or maximizing one or more of an efficiency, efficacy, and safety of a given procedure. In a typical implementation, an outside diameter of the stopper/plug may comprise about 5 mm (e.g., approximating a diameter of the canal), with the inside diameter corresponding to the diameter of the probe or fiber (e.g., 0.2 mm, 0.3 mm, 0.4 mm, etc.).

In the context of providing markings on the probe or fiber to indicate distance/depth (e.g., viewable directly or with an imager) for, as an example, aiding with the insertion of the probe or fiber into a body passage or canal (e.g., root canal), depth information my be advantageous for facilitating optimal positioning (e.g., from the bottom of the root canal) the distal or output end probe or fiber. For example, in the context of root canal preparation involving one or more of enlargement and shaping, root canal debridement and cleaning, pulp extirpation, pulpotomy for root canal therapy, and sulcular debridement, one or more of efficiency and efficacy of the procedure can be enhanced with depth-of-canal knowledge.

A file or other device can be inserted into the canal to determine the depth thereof, and then the depth information can be transferred to the probe or fiber. For example, it may be desired to insert the probe or fiber into the canal up to a point where the distal output end of the probe or fiber is 2 mm from the bottom of the canal. In such a scenario, if the root canal is determined to be 5 mm deep, as measured from the tooth crown (e.g., beginning or "top" of the canal down to the bottom of the canal), then the probe may be marked at a location 3 mm proximal of the distal output end.

Figure 6A:
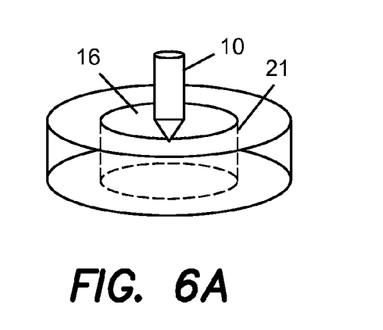
FIGS. 6A and 6B depict side-firing fiber optic tip positioning and patterning arrangements, and sequences, within a body passage such as the root canal of a tooth.
Figure 6B:
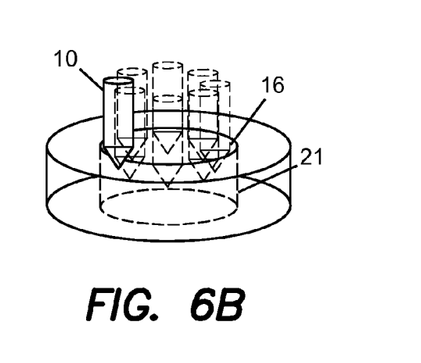

FIGS. 6A and 6B depict side-firing fiber optic positioning arrangements, patterning arrangements, and sequences, within a body passage such as the root canal 16 of a tooth. As with the concepts and exemplary particulars disclosed in connection with FIG. 2, for example, the shaped fiber optic tips 10 can comprise, for instance, structures (such as cone-shaped fiber optic tips) that deliver energy to a body passage or canal wall 21 in one or more of radial directions only, primarily radial directions, and directions at least parts of which comprise radial directions.

In addition to probes 10 being positioned a number of mm (e.g., 2 mm) from a target (e.g., bottom of a channel, such as a canal), other implementations may comprise probes 10 or fibers 10 being positioned lesser or greater distances from the target (e.g., channel or canal wall). For example, a probe or fiber 10 may be positioned in contact with the target (e.g. bottom of a channel or canal). In another exemplary implementation, such as depicted in FIG. 6A, the probe or fiber 10 may be centered within, for example, a channel to exert forces (e.g., cleaning forces) in multiple directions at the same time or at successive times (e.g., coinciding with rotation of the probe about its axis). Such a centered orientation may comprise, for example, the outputting end of a probe or fiber 10 being equally spaced from one or more of (a) sidewalls of a channel and (b) a top and bottom of the channel (e.g., canal).

Other implementations may comprise, alternatively or additionally, movement of the probe 10 distally and proximally within the canal 16 or channel as treatments (e.g., cleaning forces) are administered. For instance, for a cumulative exposure of 30 seconds a laser may be fired six times, five seconds each time, as the probe 10 is moved at a rate of 1 mm per second upward and downward within the root canal 16. In the current example or any other implementation, the probe 10 may comprise, for example, a side firing tip, such as a Z2 type (200 μm diameter and 14 mm in length) radially-emitting laser instrument tip as referenced in Prov. App. 60/961,113. An example may comprise movement of such a tip by hand up and down in the canal in a cervical-apical and apical-cervical direction at a rate of 1 mm per second (that is, 10 seconds to traverse the full 5 mm length of a canal in both directions), during which procedure the side-firing tip 10 may be kept, for example, as close to the canal wall 21 being treated as possible.

According to a further aspect of the present invention, bacterial reduction may be enhanced through use of a contact-tip or near-contact tip implementation in which side surfaces (e.g., energy-emitting side wall regions) of the fiber optic tip 10 are placed into contact, or almost into contact with, or into close proximity with, walls 21 of the passage or root canal 16. In implementations with a probe 10 having a relatively small diameter, relative to a diameter of the passage or canal 16, such as shown in FIG. 6B, implementations may comprise moving the probe 10 close to or into contact with different sidewalls 21 within the canal 16 for treatment thereof. For instance, as reflected by the schematic representation of FIG. 6B, the probe 10 may be moved in a circular direction or pattern, or in other ways, to cover part or all of a circumferential region within the canal 16 or channel as treatments (e.g., cleaning forces) are administered to the sidewall regions 21 contacted or approached by the probe 10 as it is moved.

A feature of the present invention comprises forming the stopper/plug into a user-constructible/deconstructible, user-fastenable/removable, user-adjustable/readjustable marker ("adjustable channel-depth indicator"). The stopper/plug can be affixed to the fiber or probe during a procedure, to thereby provide the marking function (e.g., at a location 3 mm proximal of the distal output end). Thus, instead of marking the probe or fiber, according to an aspect of the invention, the stopper/plug can incorporate an adjustable channel-depth indicator to indicate distance/depth (e.g., viewable, preferably, directly with the naked human eye and/or, alternatively, with an imager).

In implementations of the adjustable channel-depth indicator, one or more of a shape and a scale of the above-discussed stopper/plug is toned down (e.g., machined down) or is initially fabricated to have a reduced dimensional magnitude as compared to that of the above-described stopper/plug. Construction of the device with a reduced size or dimensional characteristic is performed to reduce the blocking capacity of the device so that, rather than a stopper/plug the device is more appropriately referenced as an adjustable channel-depth indicator. The adjustable channel-depth indicator may be formed of materials corresponding to those of the stopper/plug, such as those transparent to one or more wavelengths of electromagnetic energy (e.g., cutting laser radiation, aiming beam radiation, illuminating visible light, etc.). In an exemplary implementation, one or more of a non-opaque, transparent, clear, and see-through material may be used to form the adjustable channel depth indicator.

According to a typical embodiment, in order to reduce the canal blocking function of the adjustable channel-depth indicator, an outer diameter thereof can be reduced. As an example, compared to the above-mentioned 5 mm dimension, a substantially smaller outer diameter, such as, for example, only 0.5 mm, 1.0 mm, 1.5 mm, or 2.0 mm, may be provided, while the inside diameter can be as described above. Thus, for instance, the adjustable channel-depth indicator can comprise or possess a ring shape (e.g., structured as an O-ring) as with or resembling a shape of the above-described stopper/plug, but with a reduced outer diameter.

According to additional or alternative embodiments, an outer shape or surface of the adjustable channel-depth indicator can be altered to reduce the canal blocking function of the adjustable channel-depth indicator. For example, channels or troughs, parallel to a longitudinal axis of the probe or fiber, can be formed in the outer surface of a ring shaped adjustable channel-depth indicator.

Consequently, operation of the adjustable channel-depth indicator as a canal blocker can be attenuated to thereby enhance one or more of (a) a user's line of sight into the canal or to the distal output end of the probe or fiber and (b) delivery of a fluid (e.g., water) distally into the canal and to the distal output end of the probe or fiber.

Additionally, or as an alternative, to any of the above implementations, one or more of (a) a leading, i.e., proximal, (b) intermediate, and (c) trailing, i.e., distal, surface or edge of the adjustable channel-depth indicator can be formed to reduce friction and/or facilitate flow of fluid distally across the surface or edge.

The discussion and illustrations of Prov. App. 60/995,759 represent conceptual prototypes of sponge/sheath dispensing mechanisms according to the present invention, which mechanisms can be used to hold and position components (e.g., fluids), or components/agents/particles as defined herein, in proximity to a probe or output fiber optic tip, for dispensing, for example, of the components (e.g., biofluids, particles and/or biopowders, as disclosed herein) or components/agents during a procedure such as a treatment procedure, mode, or sub-procedure on tissue (e.g., within a canal). The sponges and sheaths can be formed, for example, in a compact (e.g., low profile) fashion for providing minimally invasive access to the surgical site of tissue (e.g., a canal, pocket, such as a periodontal pocket, or other formation of tissue).

The sponges can be formed, for example, according to process steps and/or structures as implemented, in whole or in part, in products elucidated and/or referenced on the referenced page pertaining to "K-Sponges," the entire set of products and relevant contents of which is incorporated herein by reference.

Components, such as one or more of the fluids, biofluids and biopowders (e.g., particles) disclosed herein, and/or any sub-components or agents thereof ("components/agents"), may be applied to the sponge in one or more of a powder, liquid and/or intermediate (e.g., gel or part powder/liquid) state, for subsequent release on or near a treatment site. The components/agents may be added in liquid or semi-liquid form before the sponge is formed into a compressed or low-profile shape (using, for example, any one or more parts of the above-referenced K-Sponge technology), followed by, for example, drying (e.g., dehydrating) and compressing of the sponge. Alternatively, and/or additionally, components/agents may be added in a powder, solid, semi-solid, suspended solid, dissolved or distributed solid, gel and/or powder/liquid form before, during and/or after the sponge is formed into a compressed or low-profile shape (using, for example, any one or more parts of the above-referenced K-Sponge technology).

In an implementation wherein one or more components/agents are added after the sponge has been formed into a compressed or low-profile shape, the sponge may be contacted with the component(s)/agent(s) by way of (1) dipping of the sponge into a component/agent containing solution, (2) dripping of a liquid containing the component/agent onto the sponge, or touching of the sponge with a powder of or containing the component/agent so that the component/agent attaches to a surface of and/or an interior of the sponge.

The sponges may take various shapes to be effective. These shapes can be, but are not limited to rectangular, point-end, and round-end shapes. Once placed into contact with, for example, fluid in the mouth, the sponge can be configured to expand and allow the release of biofluids or biopowders (e.g., particles) to the target site to aid the procedure.

The sheaths can be formed, for example, of a silicon type sheet of material. In other embodiments, the sheaths may be formed, in whole or in part, of, for example, gelatin and/or cellulose (e.g., alpha-cellulose). Moreover, the sheaths of the present invention may alternatively or additionally be formed, in whole or in part, of any one or more of the materials, structures, compositions or distributions of compositions, shapes, components/agents and/or steps used to make/use the sponges as described or referenced herein. The architecture of each sheath may comprise, for example: (a) a construction with one or more pores or perforations disposed anywhere along a length thereof and/or (b) a construction without pores and an opening at a distal end thereof. Either or both of the (a) and (b) constructions can be configured for dispensing the components/agents (e.g., biofluids, biopowders, particles and/or other material) as, for example, described and depicted herein. Once pressed into contact with, for example, tissue, the sheath may release biofluids or biopowders (e.g., particles) to the target site to aid the procedure.

Furthermore, components/agents may be disposed (e.g., selectively disposed) on or in only parts of the sponge or sheath, such as on and/or in one or more of: selected (e.g., partial) area(s), selected volume(s), a single side, selected pores, other surface features or indentations, all pores or other surface features or indentations, and combinations thereof.

Combination embodiments comprising hybrid sponge/sheath implementations, such as a sheath made of a sponge-like material, may also be implemented. As another example of a modification, rather than or in addition to a sponge or a sheath of sponge-like material, and/or in any embodiment described herein, an external surface of the sponge and/or sheath can be formed with surface irregularities (e.g., features) to hold components/agents (e.g., biofluids or biopowders (e.g., particles)), such as, for example, bristles.

Another application for the same sponge and/or sheath (without biofluids, particles, or biopowders) is the use of removing material from the tissue site. The sponge and/or sheath can absorb and collect dislodged materials (e.g., calculus deposits and/or removed tissue, dislodged or removed by way of, for example, the probe, fiber, other implement to which the sponge is affixed) from the site instead of using suction or other methods of removing the debris from the target.

Any of the implementations described or referenced herein may be loaded with a component/agent (e.g., biofluids, particles or biopowders) that, for example, (1) softens a component or agent on a surface of the target (e.g., a calculus deposit, and/or with such softening agent being, e.g., propylene glycol alginate (PGA)—whereby, for example, EMD dissolves in PGA at acidic pH (and/or, for example, a laser may be used to dehydrate tissue surface in order to facilitate the deposition of the EMD product)); (2) cleans the target (e.g., root) surface (e.g., an acidic component and/or etching agent, e.g., EDTA); and/or (3) medicaments such as anesthetizing agents, growth promoters, etc.

With reference to the last sheet of the drawings of Prov. App. 60/995,759, other embodiments can be fiber bundles with non cylindrical (e.g., non truncated) distal ends (e.g., angled, beveled, double-beveled, etc. distal ends) to provide different radiation outputs with varying characteristics. For such bundled embodiments one or more components/agents (e.g., a viscous component(s)) may be disposed in one or more of a central area or lumen and a peripheral area(s) of the fiber optic tip fibers, and/or may be disposed or dispersed between two or more of the fiber optic tip fibers. While the cross-section at the top of this last sheet of drawings shows a circular cross-sectional area wherein the body of each fiber bundle resemble an envelope (i.e., shape) of a cylinder, other cross-sectional shapes are also possible, such as rectangular shape or other shapes. In other embodiments, the cross-sections may correspond to flat or blade configurations of fiber bundles. Thus, as an example of a "thin blade" fiber bundle configuration, a cross section may comprise a single, straight line formed by five circles (i.e., "ooooo") corresponding to a fiber bundle formed of five fiber optic tips and having a flat cross-sectional shape (rather than the illustrated circular cross-sectional shape). As another example, which may be used as an alternative to the mentioned "thin blade" fiber bundle, a "double-thickness blade" construction may include a fiber bundle configuration, a cross section of which comprises a single, straight line formed by two rows of five circles (i.e., "ooooo") each corresponding to a fiber bundle formed to be five fiber optic tips wide and two fiber optic tips thick and having a flat cross-sectional shape (rather than the illustrated circular cross-sectional shape). Furthermore, any embodiment described or referenced may comprise one or more of the fiber optic tips (e.g., of a given fiber bundle) having a shape other than that of a regular, conventional, cylindrically-shaped fiber optic tip end (i.e., a truncated fiber end corresponding or identical to the shape of a cylinder). For example, one or more of the fiber optic tips may comprise a planar, beveled output end of any orientation and/or may comprise an output end that may be wholly or partially spherical, rounded, jagged, chiseled or otherwise shaped for altering a light-intensity output distribution thereof, as compared to a truncated fiber end.

In another implementation, a user could dip the fiber or bundled fiber construction into a component or medicament (e.g., any biofluids, particles or biopowders as described herein), before use thereof. Any of such constructions may be implemented as a single fiber, as well, as distinguished from a fiber bundle. Also, the "sheath" may be embodied, in addition and/or as an alternative to any of the implementations described herein, as a side cannula as elucidated in the bottom center cross-sectional schematic provided on the last sheet of drawings (e.g., for holding/dispensing components (e.g., biofluids, biopowders or particles) along length thereof); thus, a single or an additional cannula or cannulas can be provided on the side each with a single output at its distal end and/or with one or more output apertures along a length thereof, alone or in addition to, for example, a central cannula-type (e.g., lumen) structure for holding/dispensing components (e.g., biofluids, biopowders or particles) along length thereof.

According to certain features of the invention, a bubble may be formed just on a side of the probe (e.g., with a side firing output end). In other certain features of the invention, a bubble may be formed just at the distal end, side, or surface of the probe. As for other aspects, one or more bubbles may be formed at one or more of (a) the distal end, side, or surface, only, (b) a sidewall location and (c) a plurality of different sidewall locations (e.g., corresponding to one or multiple bubbles) Any of these bubbles may be formed with different liquids and/or different radiation characteristics (e.g., wavelengths, intensities, durations, sequences, spatial or time mixing with other radiation, etc.). A bubble can be created with radiation having first characteristics (e.g., wavelength, pulse, etc.) and then, for example, another one or more radiations having one or more different characteristics (e.g., wavelength, or pulse, etc.) can be used, instead of or in addition to (overlapping in time and or space, and/or alternating in whole or in part temporally and/or spatially) the first radiation. For instance, wavelength(s) of the first radiation may be minimally absorbed by (e.g., transparent to) a surrounding aqueous liquid so as to form the bubble, while wavelength(s) of the second radiation or radiations may be wholly, partially, or minimally absorbed by the liquid for one or more of (a) whole or partial maintenance of the dynamic, gaseous bubble and (b) operation/manipulation/treatment, such as cutting, on the target within (e.g., partially or substantially entirely) the environment of the bubble.

Item (b) may even comprise, for example, removal of liquid from an immediate vicinity (e.g., directly adjacent to) the target surface such as with the implementation of a near IR wavelength (e.g., 810 nm, 790 nm, 940 nm, and other wavelengths in or near the range) so as to facilitate generation by the radiation on the target without excessive, operation-degrading cooling at the point of radiation impact with the target.

The surrounding aqueous liquid may be blood, or in another implementation, liquid, and/or may comprise other liquid(s).

In some aspects, a bubble can be created with one wavelength (e.g., in pulses of near IR radiation that is highly absorbed by water) to create and begin expanding a bubble, and then another wavelength (e.g., in pulses of near IR radiation, such as from a diode, that is not so absorbed by water)

can be used, in addition or instead, for operation on or affecting one or more of the bubble and the target. Thus, once the bubble has been opened with the first radiation, and then expanded (with the first and/or second radiation) to form a gaseous pathway from the radiation emitting end of the probe to the target, the target can then be accessed and treated (e.g., with one or more additional radiations and/or with one or more of the first and second radiations, in any combination or distribution).

Furthermore, regarding (b), the second radiation(s) such as from a near IR wavelength (e.g., from a diode) can provide a first target operation of opening, altering, or disrupting, to any degree, tissue at the surface to prepare the surface for striking or treatment by an IR laser during a second target operation, and then the first and second target operations can be repeated in any variation, pattern, form, combination and/or permutation, for any number of times. For instance, adjustment can be made so that the IR radiation is (1) relatively low (e.g., non-destructive to the tissue) radiation for one or more of opening soft tissue and/or making it more (a) penetrable by way for example of the application of low level light therapy and/or (b) tolerant to pain whereby tissue is just conditioned for cutting (e.g., conditioned whereby nerve path changes can raise pain threshold for an analgesic effect, such as in a cavity preparation procedure) and/or (2) at a relatively high level to kill bacteria or modify the target tissue structure such as to melt, close or seal dentinal tissue (e.g., remodel it), coagulate fluids, or close pores.

Is some aspects, pulsed visible light can be provided for imaging whereby the bubble path can be used to provide a more visible line of sight for imaging the target during or between procedures. Combinations of visible and cutting wavelength can be used whereby, for example, the cutting light can be timed to strobe at times (e.g., at regular intervals and/or between cutting) when particulates in the bubble are at reduced levels and/or at reduced levels in a given line of sight (from the imaging fiber optic tip to the target) for better visibility.

According to certain implementations, laser radiation is output from a power or treatment fiber (e.g., forming or within a probe), and is directed, for example, into fluid (e.g., an air and/or water spray or an atomized distribution of fluid particles from a water connection and/or a spray connection near an output end of the handpiece) that is emitted from a fluid output of a handpiece above a target surface (e.g., one or more of tooth, bone, cartilage and soft tissue). The fluid output may comprise a plurality of fluid outputs, concentrically arranged around a power fiber, as described in, for example, App. 11/042,824 and Prov. App. 60/601,415. The power or treatment fiber may be coupled to an electromagnetic radiation source comprising, for example, one or more of a wavelength within a range from about 2.69 to about 2.80 microns and a wavelength of about 2.94 microns. In certain implementations the power fiber may be coupled to one or more of a diode, an Er:YAG laser, an Er:YSGG laser, an Er, Cr:YSGG laser and a CTE:YAG laser, and in particular instances may be coupled to one of an Er, Cr:YSGG solid state laser having a wavelength of about 2.789 microns and an Er:YAG solid state laser having a wavelength of about 2.940 microns. An apparatus including corresponding structure for directing electromagnetic radiation into an atomized distribution of fluid particles above a target surface is disclosed, for example, in the below-referenced U.S. Pat. No. 5,574,247, which describes the impartation of laser radiation into fluid particles to thereby apply disruptive forces to the target surface.

According to exemplary embodiments, operation in one or more of a gaseous and a liquid environment (e.g., within a channel or canal) can comprise a laser (e.g., an Er, Cr:YSGG solid state laser) having: a repetition rate of about 10 or 20 Hz or, in other implementations (e.g., for one or more of a relatively larger channel and a more calcified or stubborn target) about 30 to 50 Hz; and an energy per pulse from about 2 to 60 mJ, or in other embodiments (e.g., for one or more of a relatively larger channel and a more calcified or stubborn target) greater than 60 mJ such as levels up to about 150 mJ or 200 mJ. The higher frequencies are believed potentially to enhance an efficiency or efficacy of one or more of enlargement and shaping, root canal debridement and cleaning, pulp extirpation, pulpotomy for root canal therapy, sulcular debridement, and others. For exemplary channel transverse-widths (e.g., diameters) greater than 25 microns, such as those ranging from about 250 to 450, or 600, microns, probe or fiber diameters may range from about 10 to 450 microns, or from about 25 to 300 microns. For channels comprising one or more of a relatively large diameter (e.g., about 400 or 450 to about 600, or more, microns) and a more calcified or stubborn target, probe or fiber diameters may range from about 300 to 400, or 500, or 600, or more, microns. An example may comprise a 200 to 300 micron fiber, outputting radiation at about 60 mJ/pulse and 50 Hz, in a 250 to 600 micron wide canal. Probe or fiber output regions may comprise, for example, one or more of the structures and functions as disclosed in, for example, any of Prov. App. 61/012,446, Prov. App. 60/995,759, Prov. App. 60/961,113, application Ser. No. 11/800,184, Int. App. PCT/US08/52106, application Ser. No. 11/330,388, application Ser. No. 11/033,441, and U.S. Pat. No. 7,270,657. As an example, the outputting distal end of a probe or fiber may comprise a conical shape having a full angle of about 45 to 60 degrees and/or may comprise one or more beveled surfaces.

By way of the disclosure herein, a laser has been described that can output electromagnetic radiation useful to diagnose, monitor and/or affect a target surface. In the case of procedures using fiber optic tip radiation, a probe can include one or more power or treatment fibers for transmitting treatment radiation to a target surface for treating (e.g., ablating) a dental structure, such as within a canal. In any of the embodiments described herein, the light for illumination and/or diagnostics may be transmitted simultaneously with, or intermittently with or separate from, transmission of the treatment radiation and/or of the fluid from the fluid output or outputs.

Corresponding or related structure and methods described in the following patents assigned to BIOLASE Technology, Inc., are incorporated herein by reference in their entireties, wherein such incorporation includes corresponding or related structure (and modifications thereof) in the following patents which may be, in whole or in part, (i) operable with, (ii) modified by one skilled in the art to be operable with, and/or (iii) implemented/used with or in combination with, any part(s) of the present invention according to this disclosure, that of the patents or below applications, and the knowledge and judgment of one skilled in the art.

Such patents include, but are not limited to, U.S. Pat. No. 7,356,208 entitled Fiber detector apparatus and related methods; U.S. Pat. No. 7,320,594 entitled Fluid and laser system; U.S. Pat. No. 7,303,397 entitled Caries detection using timing differentials between excitation and return pulses; U.S. Pat. No. 7,292,759 entitled Contra-angle rotating handpiece having tactile-feedback tip ferrule; U.S. Pat. No. 7,290,940 entitled Fiber tip detector apparatus and related methods; U.S. Pat. No. 7,288,086 entitled High-efficiency, side-pumped diode laser system; U.S. Pat. No. 7,270,657 entitled Radiation emitting apparatus with spatially controllable output energy distributions; U.S. Pat. No. 7,261,558 entitled Electromagnetic radiation emitting toothbrush and dentifrice system; U.S. Pat. No. 7,194,180 entitled Fiber detector apparatus and related methods; U.S. Pat. No. 7,187,822 entitled Fiber tip fluid output device; U.S. Pat. No. 7,144,249 entitled Device for dental care and whitening; U.S. Pat. No. 7,108,693 entitled Electromagnetic energy distributions for electromagnetically induced mechanical cutting; U.S. Pat. No. 7,068,912 entitled Fiber detector apparatus and related methods; U.S. Pat. No. 6,942,658 entitled Radiation emitting apparatus with spatially controllable output energy distributions; U.S. Pat. No. 6,829,427 entitled Fiber detector apparatus and related methods; U.S. Pat. No. 6,821,272 entitled Electromagnetic energy distributions for electromagnetically induced cutting; U.S. Pat. No. 6,744,790 entitled Device for reduction of thermal lensing; U.S. Pat. No. 6,669,685 entitled Tissue remover and method; U.S. Pat. No. 6,616,451 entitled Electromagnetic radiation emitting toothbrush and dentifrice system; U.S. Pat. No. 6,616,447 entitled Device for dental care and whitening; U.S. Pat. No. 6,610,053 entitled Methods of using atomized particles for electromagnetically induced cutting; U.S. Pat. No. 6,567,582 entitled Fiber tip fluid output device; U.S. Pat. No. 6,561,803 entitled Fluid conditioning system; U.S. Pat. No. 6,544,256 entitled Electromagnetically induced cutting with atomized fluid particles for dermatological applications; U.S. Pat. No. 6,533,775 entitled Light-activated hair treatment and removal device; U.S. Pat. No. 6,389,193 entitled Rotating handpiece; U.S. Pat. No. 6,350,123 entitled Fluid conditioning system; U.S. Pat. No. 6,288,499 entitled Electromagnetic energy distributions for electromagnetically induced mechanical cutting; U.S. Pat. No. 6,254,597 entitled Tissue remover and method; U.S. Pat. No. 6,231,567 entitled Material remover and method; U.S. Pat. No. 6,086,367 entitled Dental and medical procedures employing laser radiation; U.S. Pat. No. 5,968,037 entitled User programmable combination of atomized particles for electromagnetically induced cutting; U.S. Pat. No. 5,785,521 entitled Fluid conditioning system; and U.S. Pat. No. 5,741,247 entitled Atomized fluid particles for electromagnetically induced cutting.

Also, the above disclosure and referenced items, and that described on the referenced pages, are intended to be operable or modifiable to be operable, in whole or in part, with corresponding or related structure and methods, in whole or in part, described in the following published applications and items referenced therein, which applications are listed as follows: App. Pub. 20080125677 entitled Methods for treating hyperopia and presbyopia via laser tunneling; App. Pub. 20080125676 entitled Methods for treating hyperopia and presbyopia via laser tunneling; App. Pub. 20080097418 entitled Methods for treating eye conditions; App. Pub. 20080097417 entitled Methods for treating eye conditions; App. Pub. 20080097416 entitled Methods for treating eye conditions; App. Pub. 20080070185 entitled Caries detection using timing differentials between excitation and return pulses; App. Pub. 20080065057 entitled High-efficiency, side-pumped diode laser system; App. Pub. 20080065055 entitled Methods for treating eye conditions; App. Pub. 20080065054 entitled Methods for treating hyperopia and presbyopia via laser tunneling; App. Pub. 20080065053 entitled Methods for treating eye conditions; App. Pub. 20080033411 entitled High efficiency electromagnetic laser energy cutting device; App. Pub. 20080033409 entitled Methods for treating eye conditions; App. Pub. 20080033407 entitled Methods for treating eye conditions; App. Pub. 20080025675 entitled Fiber tip detector apparatus and related methods; App. Pub. 20080025672 entitled Contra-angle rotating handpiece having tactile-feedback tip ferrule; App. Pub. 20080025671 entitled Contra-angle rotating handpiece having tactile-feedback tip ferrule; App. Pub. 20070298369 entitled Electromagnetic radiation emitting toothbrush and dentifrice system; App. Pub. 20070263975 entitled Modified-output fiber optic tips; App. Pub. 20070258693 entitled Fiber detector apparatus and related methods; App. Pub. 20070208404 entitled Tissue treatment device and method; App. Pub. 20070208328 entitled Contra-angel rotating handpiece having tactile-feedback tip ferrule; App. Pub. 20070190482 entitled Fluid conditioning system; App. Pub. 20070184402 entitled Caries detection using real-time imaging and multiple excitation frequencies; App. Pub. 20070104419 entitled Fiber tip fluid output device; App. Pub. 20070060917 entitled High-efficiency, side-pumped diode laser system; App. Pub. 20070059660 entitled Device for dental care and whitening; App. Pub. 20070054236 entitled Device for dental care and whitening; App. Pub. 20070054235 entitled Device for dental care and whitening; App. Pub. 20070054233 entitled Device for dental care and whitening; App. Pub. 20070042315 entitled Visual feedback implements for electromagnetic energy output devices; App. Pub. 20070014517 entitled Electromagnetic energy emitting device with increased spot size; App. Pub. 20070014322 entitled Electromagnetic energy distributions for electromagnetically induced mechanical cutting; App. Pub. 20070009856 entitled Device having activated textured surfaces for treating oral tissue; App. Pub. 20070003604 entitled Tissue coverings bearing customized tissue images; App. Pub. 20060281042 entitled Electromagnetic radiation emitting toothbrush and dentifrice system; App. Pub. 20060275016 entitled Contra-angle rotating handpiece having tactile-feedback tip ferrule; App. Pub. 20060241574 entitled Electromagnetic energy distributions for electromagnetically induced disruptive cutting; App. Pub. 20060240381 entitled Fluid conditioning system; App. Pub. 20060210228 entitled Fiber detector apparatus and related methods; App. Pub. 20060204203 entitled Radiation emitting apparatus with spatially controllable output energy distributions; App. Pub. 20060142743 entitled Medical laser having controlled-temperature and sterilized fluid output; App. Pub. 20060099548 entitled Caries detection using timing differentials between excitation and return pulses; App. Pub. 20060043903 entitled Electromagnetic energy distributions for electromagnetically induced mechanical cutting; App. Pub. 20050283143 entitled Tissue remover and method; App. Pub. 20050281887 entitled Fluid conditioning system; App. Pub. 20050281530 entitled Modified-output fiber optic tips; App. Pub. 20040106082 entitled Device for dental care and whitening; App. Pub. 20040092925 entitled Methods of using atomized particles for electromagnetically induced cutting; App. Pub. 20040091834 entitled Electromagnetic radiation emitting toothbrush and dentifrice system; App. Pub. 20040068256 entitled Tissue remover and method; App. Pub. 20030228094 entitled Fiber tip fluid output device; App. Pub. 20020149324 entitled Electromagnetic energy distributions for electromagnetically induced mechanical cutting; and App. Pub. 20020014855 entitled Electromagnetic energy distributions for electromagnetically induced mechanical cutting.

All of the contents of the preceding published applications are incorporated herein by reference in their entireties.

The above-described embodiments have been provided by way of example, and the present invention is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. As iterated above, any feature or combination of features described and referenced herein are included within the scope of the present invention provided that the features included in any such combination are not mutually inconsistent as will be apparent from the context, this specification, and the knowledge of one of ordinary skill in the art. For example, any of the radiation outputs (e.g., lasers), any of the fluid outputs (e.g., water outputs), and any conditioning agents, particles, agents, etc., and particulars or features thereof, or other features, including method steps and techniques, may be used with any other structure(s) and process described or referenced herein, in whole or in part, in any combination or permutation as a non-equivalent, separate, non-interchangeable aspect of this invention. Accordingly, the present invention is not intended to be limited by the disclosed embodiments, but is to be defined by such embodiments and by reference to the following claims.

What is claimed is:

1. An endodontic probe, comprising:
   an electromagnetic radiation emitting fiber optic tip having a distal end and a radiation emitting region disposed proximally of the distal end;
   a porous structure encompassing a region of the fiber optic tip excluding the radiation emitting region, the porous structure being loaded with one or more of biologically-active particles, cleaning particles, biologically-active agents, and cleaning agents that are structured to be delivered from the porous structure onto tissue; and
   a seal disposed over at least part of the porous structure, the seal being constructed to be pealed away from the porous structure.

2. The endodontic probe as set forth in claim 1, wherein the porous structure encompasses a region of the fiber optic tip adjacent to the radiation emitting region.

3. The endodontic probe as set forth in claim 1, wherein the porous structure is a porous wall which is an integral, non-removable part of the fiber optic tip.

4. The endodontic probe as set forth in claim 1, wherein the porous structure covers a region of the fiber optic tip distally of the radiation emitting region.

5. The endodontic probe as set forth in claim 1, wherein the porous structure is secured to and can be retracted and removed from the endodontic probe while inside of a dentinal canal.

6. The endodontic probe as set forth in claim 1, wherein the electromagnetic radiation emitting fiber optic tip is configured to be coupled to an infrared laser.

7. The endodontic probe as set forth in claim 1, wherein the electromagnetic radiation emitting fiber optic tip is configured to be coupled to a near-infrared laser.

8. The endodontic probe as set forth in claim 1, wherein the electromagnetic radiation emitting fiber optic tip is configured to be coupled to an infrared laser and a near-infrared diode laser, the infrared laser being configured to maintain a bubble in a fluid environment while the diode laser treats a surface within or near a boundary of the bubble.

9. The endodontic probe as set forth in claim 8, wherein the treating of a surface by the diode laser comprises heating or ablating the surface by the diode laser.

10. The endodontic probe as set forth in claim 1, wherein the endodontic probe comprises a capability for outputting, from the radiation emitting region, one or more of a first radiation and a second radiation.

11. The endodontic probe as set forth in claim 10, the first radiation and the second radiation being controlled to be output in one or more of a simultaneous, alternating, automatically sequenced, and manually sequenced, fashion.

12. The endodontic probe as set forth in claim 1, wherein the electromagnetic radiation emitting fiber optic tip is configured to be coupled to in infrared laser and a diode.

13. The endodontic probe as set forth in claim 12, the infrared laser being configured for emitting a first radiation and the diode being configured for emitting a second radiation differing from the first radiation by at least one detectable, quantifiable radiation-descriptive parameter.

14. The endodontic probe as set forth in claim 13, wherein the endodontic probe is constructed to be coupled to and to be immediately operational with one or more of an infrared laser and a near-infrared laser.

15. The endodontic probe as set forth in claim 1, the endodontic probe being constructed to emit a first radiation that is highly absorbed by a biologically compatible liquid within a canal and, simultaneously or substantially simultaneously, to emit a second radiation that is not highly absorbed by the liquid.

16. The endodontic probe as set forth in claim 1, wherein:
   the endodontic probe is configured to output combinations of a first radiation and a second radiation; and
   one or more of a temporal output characteristic and a spatial output characteristic is varied between the outputted first radiation and the outputted second radiation.

17. An endodontic probe comprising:
   an electromagnetic radiation emitting fiber optic tip having a distal end and a radiation emitting region disposed proximally of the distal end;
   a porous structure encompassing a region of the fiber optic tip excluding the radiation emitting region, the porous structure being loaded with one or more of biologically-active particles, cleaning particles, biologically-active agents, and cleaning agents that are structured to be delivered from the porous structure onto tissue; and
   a seal disposed over at least part of the porous structure, the seal being adhesively secured to the endodontic probe.

18. An endodontic probe comprising:
   an electromagnetic radiation emitting fiber optic tip having a distal end and a radiation emitting region disposed proximally of the distal end;
   a porous structure encompassing a region of the fiber optic tip excluding the radiation emitting region, the porous structure being loaded with one or more of biologically-active particles, cleaning particles, biologically-active agents, and cleaning agents that are structured to be delivered from the porous structure onto tissue; and
   a seal disposed over at least part of the porous structure, the seal being constructed to be removed while within a dentinal canal by operation of one or more of dissolving and melting.

* * * * *